US006531574B1

(12) United States Patent
Essex et al.

(10) Patent No.: US 6,531,574 B1
(45) Date of Patent: Mar. 11, 2003

(54) T-LYMPHOTROPHIC VIRUS (75) Inventors: Myron E. Essex, Sharon; Phyllis J. Kanki, Carlisle, both of MA (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 08/378,872

(22) Filed: Jan. 24, 1995

Related U.S. Application Data (63) Continuation of application No. 07/984,231, filed on Dec. 1, 1992, now abandoned, which is a continuation of application No. 07/658,460, filed on Feb. 22, 1991, which is a continuation of application No. 07/538,680, filed on Jun. 15, 1990, which is a continuation of application No. 06/844,072, filed on Mar. 26, 1986, which is a continuation-in-part of application No. 06/798,126, filed on Nov. 14, 1985, now abandoned.

(51) Int. Cl.[7] ................................................ C07K 1/00
(52) U.S. Cl. ..................... 530/350; 435/41; 435/71.1; 435/235.1; 435/236; 435/239; 435/372; 530/395; 530/826
(58) Field of Search ........................ 435/974, 41, 71.1, 435/235.1, 236, 239, 372; 530/350, 395, 826

(56) References Cited

U.S. PATENT DOCUMENTS 4,725,669 A * 2/1988 Essex et al. ................ 530/395

OTHER PUBLICATIONS

Mulder, "A Case of Mistaken Non–Identity", Nature, vol. 331(Feb. 18, 1988), pp. 562–563.*
Kestler et al. "Comparison of Simian Immunodeficiency Virus Isolates", Nature, vol. 331(Feb. 18, 1988), pp. 619–622.*
Remold–O'Donnell, "Macrophage Component gp–160 a Major Trypsin Sensitive Surface Glyco Protein", Journal of Experimental Medicine, vol. 152, No. 6(1980), pp. 1699–1708. R850.J6. Abstract Only.*
Tokuyama et al., "Cell Surface Major Glyco Protein of Balb–c Mouse Plasma Cytoma 58–8 Cells", Journal Of National Cancer Institute, vol. 61, No. 1(1978), pp. 203–208. R850.J6. Abstract Only.*
Owens et al., "A Minor Sialo Glyco Protein of Human Erythrocyte Membrane", Archives of Biochemistry and Biophysics, vol. 204, No.1(1980), pp. 247–254. QP501.A77.*
Costantino–Ceccarini et al., "Further Characterization of Hela S–3 Plasma Membrane Ghosts", Journal of Cellular Biology, vol. 77, No. 2(1978), pp. 448–463. QH301.J677. Abstract Only.*
Kestler, H., et al., Nature, 331 : 619–621 (1988).*
Essex, M., et al., Nature, 331 : 621–622 (1988).*
Mulder, C., Nature, 331 : 562–563 (1988).*
Desrosiers, R., et al., Nature, 327 : 107 (1987).*
Kanki et al., Science, 228 : 1199–1201, Jun. 7, 1985.*
Robey et al., Science, 228 : 593–595, May 3, 1985.*
Wong–Staal et al., Science, 229 : 759–762, Aug. 23, 1985.*
Hahn et al., Proc. Nat'l. Acad. Sci. USA, 82 : 4813–4817 (1985).*
Yamamoto et al., J. Gen. Vir., 65 : 2259–2264 (1984).*
Daniel et al., Science; 228 : 1201–1204, Jun. 7, 1985.*
Kanki et al., Science, 230 : 951–954, Nov. 22, 1985.*
Kanki et al., Science, 232 : 238–243, Apr. 11, 1986.*
Ishikawa et al. (1988) Aids 2:3803–388.
Marx (1988) Res. News:1243.
Chalifoux et al. (1984) Lab. Invest. 51:22–26.
Dryden (Nov. 24, 1985) Washington Post.
Saltus, Boston Globe:1, 30.
King et al. (1983) A.J.P. 113: 382–388.
Henrickson et al. (1984) Lab. Animal Sci. 34: 140–145.
Henrickson et al. (1983) Lancet: 388–390.
Letvin et al. (1983) P.N.A.S. USA 80: 2718–2722.
Hefti et al. (1983) Virology 127: 309–319.
Daniel et al. (1984) Science 223: 602–605.
Desrosiers et al. (1985) J. Virol. 54: 552–560.
Bryant et al. (1986) J.N.C.I. 77: 957–965.
Hunt et al. (1983) P.N.A.S. USA 80: 5085–5089.
Stromberg et al. (1984) Science 224: 289–292.
Giddens et al. (1985) A.M.P. 119: 253–263.
London et al. (1983) Lancet: 869–873.
Gravell et al. (1984) Science 223: 74–76.
Manning et al. (1974) Lab. Animal Sci. 24: 204–210.
Cleveland, D.W. et al., J. Biol. Chem. 252:1102–1106 (1977).
Morgan, M.A. et al., J. Virol. 46:177–186 (1983).
Snyder, H.W. et al., Cold Spring Harbor Symposium Quant. Biol. XLIV:787–799 (1980).
J.S. Allan, et al. Science, 228:1091–1094 (1985).
European Search Report, EP 86 90 7154, (1988).
Montagnier, et. al., Virology 144:283–289 (1985).
Kanki et al., The Lancet 1330–1332 (Jun. 8, 1985).
Poiesz et al., Proc.Nat'l.Acad.Sci., USA, vol. 77, p. 7415 (1980).

(List continued on next page.)

Primary Examiner—Jeffrey Stucker
(74) Attorney, Agent, or Firm—McDonnell Boehnen Hulbert & Berghoff (57) ABSTRACT

A substantially pure polypeptide having at least one antigenic determinant that is substantially identical to an antigenic determinant of a protein from a cell line infected with a specified virus that has been deposited with the ATCC, the protein being selected from: a) a glycoprotein having a molecular weight (m.w.) of about 160,000 daltons; a glycoprotein having a m.w. of about 120,000 daltons; a gag protein having a m.w. of about 55,000 daltons; a gag protein having a m.w. of about 24,000 daltons; and a glycoprotein having a m.w. of about 32,000 daltons. Also disclosed are various methods of immunoassay using that peptide or antibodies raised to it. Finally, immunoassays for simian specimens are disclosed using peptides that are immunologically cross-reactive with the above-described peptide, or antibodies thereto.

13 Claims, 6 Drawing Sheets

OTHER PUBLICATIONS

Guo et al., Science, vol. 223, p.1195 (1984).
Tsujimoto et al., Virology, vol. 144, p. 59 (1985).
Popovic et al., Science, vol. 224, p. 497 (1984).
Salahuddin et al., Science, vol. 224, p. 500 (1984).
Schupbach et al., Science, vol. 224, p. 503 (1984).
Sarngadharn et al., Science, vol. 224, p. 506 (1984).

* cited by examiner

T-LYMPHOTROPHIC VIRUS

This application is a continuation of application Ser. No. 07/538,680, filed Jun. 15, 1990, which is a continuation of Ser. No. 06/844,072, filed Mar. 26, 1986, which is a continuation-in-part application of Ser. No. 06/798,126, filed Nov. 14, 1985 now Abn.

This application is a continuation of application Ser. No. 07/658,460, filed Feb. 22, 1991.

This application is a continuation of application Ser. No. 07/984,231, filed Dec. 1, 1992 now ABN.

This application is a continuation-in-part of our commonly owned pending application Ser. No. 798,126, filed Nov. 14, 1985, which is hereby incorporated by reference.

This invention was made with Government support, including NIH research grants CA37466 and CA18216, and National Research Service Award ST32 CA9382. The Government has certain rights in the invention.

BACKGROUND OF THE INVENTION

This invention relates to primate T-lymphotropic viruses, as well as assays for such viruses and substances used in those assays.

A group of closely related human retroviruses that preferentially infect helper T-lymphocytes have been designated human T-lymphotropic viruses (HTLV). One type of HTLV, designated HTLV-I, has been linked with the development of adult T-cell leukemia/lymphoma (Poiesz et al. (1980) Proc. Nat'l. Acad. Sci. USA 77:7415). A virus related to HTLV-I has been reported in non-human primates, specifically Asian and African Old World primate species, but not New World primates and prosimians. The primate viruses from baboons, African green monkeys, and Macaca species are related to, yet distinct from, HTLV-I. Guo et al. (1984) Science 223:1195; Tsujimoto et al. (1985) Virology 144:59.

Another type of HTLV, designated variously as HTLV-III, or Lymphadenopathy Associated Virus ("LAV" or "ARV") is the prototype virus from patients with acquired immune deficiency syndrome (AIDS) (Popovic et al. (1984) Science 224:497; Salahuddin et al. (1984) Science 224:500; Schupbach et al. (1984) Science 224:503; Sarngadharn et al. (1984) Science 224:506). Various antigenic proteins from HTLV-III infected cells have been reported, including:

1) a 55 kd gag polyprotein (p55) which yields a 24 kd protein (p24) as the major virus core protein, and a 17 kd phosphoprotein (pp17) (Schupbach et al. (1984) Science 224:503–505); and 2) an envelope glycoprotein (gp160) which gives rise to a 120 kd glycoprotein (gp120) at its amino terminus (Essex and Lee, U.S. Ser. No. 670,361, filed Nov. 9, 1984, and a continuation-in-part thereof filed Nov. 7, 1985, both of which are hereby incorporated by reference).

SUMMARY OF THE INVENTION

The discovery and characterization of the polypeptide of this invention are important in several respects. First, the polypeptides provide a source of antigenic determinants that are generally useful in assays of simian or human specimens, as described below. Second, African green monkeys, are used for research and development of a variety of biological reagents; for example African green monkey tissue is used in the production of oral polio vaccine. It is desirable to reduce the chance (however unlikely) that an AIDS-like disease could be transmitted inadvertently in polio vaccine or other products produced from STLV-III-infected animal tissue. Third, a vaccine based on the proteins could protect against AIDS Peptides Having Antigenic Determinants According to the Invention, And Assays Using Them A first aspect of the invention generally features a substantially pure polypeptide having at least one antigenic determinant that is substantially identical to an antigenic determinant of a protein from a cell line infected with a virus deposited with the ATCC as CRL 8942, CRL 8943, or VR 2129, the protein being selected from: a glycoprotein having a molecular weight (m.w.) of about 160,000 daltons; and a glycoprotein having a m.w. of about 120,000 daltons. daltons; a gag protein having a m.w. of about 55,000 daltons; a gag protein having a m.w. of about 24,000 daltons; and a glycoprotein having a m.w. of about 32,000. By "a polypeptide having an antigenic determinant that is substantially identical to a protein antigenic determinant" is meant a polypeptide comprising an antigenic determinant which: a) in common with the protein antigenic determinant, will react with a given antibody; and b) is derived either by i) isolating the naturally produced protein or a fragment of it; or ii) synthesizing (e.g. by expression of DNA such as by the general method of Chang et al. (1985) Nature 315:151, or chemical synthesis) an amino acid sequence identical to the protein antigenic determinant. As demonstrated below, the polypeptides of the invention are immunologically cross-reactive with HTLV-III cell proteins, but the reaction of a polypeptide of the invention with a given antibody may vary in comparison to the reaction of the corresponding HTLV-III protein with the same antibody. Therefore, determinants of the polypeptides of the invention are not substantially identical to HTLV-III determinants.

Preferably, the polypeptide antigenic determinant is substantially identical to an antigenic determinant of a protein expressed in a cell line infected with STLV-III. Preferably, the polypeptide is one of the proteins listed above, or a fragment thereof; most preferably, the polypeptide is a gp32 or a gp160 or gp120 glycoprotein in the glycosylated or unglycosylated form. Also preferably, the polypeptide is not substantially cross-reactive with the HTLV-III/LAV glycoprotein p41; and the polypeptide antigenic determinant is more strongly reactive with an antibody capable of reacting with a determinant of a glycoprotein of one of the deposited strains than with an HTLV-III glycoprotein determinant. Other useful polypeptides which have the necessary immunogenic determinants include synthetic polypeptides.

The above described polypeptides of the first aspect of the invention are useful, among other things, for assaying for the presence of antibodies to T-lymphotropic viral antigens, by incubating a specimen with the polypeptide and determining whether or not an immunocomplex is formed. Also, the above-described polypeptides can be used to raise an antibody that is useful for assaying a biological specimen (e.g., human or simian) for the presence of an antigenic determinant that is immunologically cross-reactive with a determinant of one of the four proteins listed above. The assay is performed by incubating the specimen with the antibody thus raised and determining whether an immunocomplex is formed. The determinants to be assayed may occur on the stated proteins themselves or on other polypeptides. They may be in free circulation in the body fluids or in lymphocytes. The assay can be carried out by known immunoassay methods, using antibodies, monoclonal or polyvalent, having immune reactivity with the antigenic determinants found on the stated proteins. For example, competitive immunoassays or immunometric (sandwich) assays can be used. The assays of the first aspect are preferably performed on simian specimens, but they can also be performed on human specimens.

Vaccines

In another aspect, the invention features a vaccine comprising the above described deposited virus or a subunit protein or polypeptide thereof, such as the gp120, or gp160 or a peptide fraction of those molecules that reacts with HTLV-III. This could be presented in a pharmaceutically acceptable carrier. Vaccine could also comprise proteins from cells infected with the deposited virus or an altered form thereof.

Other features and advantages of the invention will be apparent from the following description of the preferred embodiment and from the claims.

DESCRIPTION OF THE PREFERRED EMBODIMENT

We first briefly describe the drawings.

I. Drawings

II. Obtaining the proteins

The proteins are isolated from cell lines infected with the deposited virus. The reference infected cell lines were derived from co-cultivation of infected lymphocytes and HUT-78 cells. The HUT 78 cell line is a well-characterized mature human T-cell line reported in Gazdar et al. Blood 55:409 (1980); Poiesz et al. Proc. Nat'l. Acad. Sci. USA 77:6815 (1980). Two such HUT-78/infected cell lines have been deposited with the American Type Culture Collection under ATCC Nos. CRL 8942, 8943 IV/HUT-78 cell line is deposited with the ATCC as VR 2129. Relevant proteins could be genetically mapped, and the proteins could then be made by genetic engineering.

The preferred proteins are the gp160/120 glycoproteins, which have a molecular weight of approximately 120,000 daltons and 160,000 daltons as determined by sodium dodecyl sulfate polyacrylamide gel electrophoresis (SDS/PAGE), gel electrophoresis, and the proteins are soluble in SDS buffer consisting of 0.15 M sodium chloride, 0.05 M Tris hydrochloride pH 7.2, 1% Triton X-100, 1% sodium deoxycholate, 0.1% sodium dodecylsulfate, and 1 mM phenylmethylsulfonyl fluoride. Triton X-100 is a nonionic detergent (octylphenoxy polyethoxy (9–10) ethanol). The unglycosylated moiety of the 160,000 dalton glycoprotein has a molecular weight of approximately 90,000 daltons and is immunogenic, sharing some antigenic determinant or determinants with the glycoproteins themselves.

A variety of other cell lines can be infected with the deposited virus; among them can be mentioned H9 cells, NC37 cells, Molt 3 cells, Molt 4 cells, and CEM cells. It may be that the exact sizes of the novel glycoproteins are slightly different in different lines; however, the common immunologically cross-reactive portion of the glycoproteins is the same regardless of cell line, since it is a protein induced by the deposited virus. Thus, any cell which harbors the virus may be an appropriate source for the novel glycoproteins.

In order to obtain the protein from any infected cells carrying the virus, the cells are metabolically labelled (e.g. with $^{35}$S-cysteine) and immunoprecipitated with antisera obtained from STLV-III infected animals or HTLV-IV infected humans. The glycoproteins can be prepared with lentil-lectin affinity chromatography from infected cell lysate and subjected to SDS/PAGE. For example, the glycoproteins are present in cell HUT 78 cell lines infected with the deposited virus. HUT 78 cells can be infected with fresh virus isolates from infected animals or humans. The glycoproteins can readily be separated from these cell lines by lysis thereof and SDS gel electrophoresis.

III. Assays

Purified and isolated glycoproteins or any antigen immunologically cross-reactive therewith can be employed as a standard antigen in any conventional assay procedure for detection of antibodies specific thereto in biological specimens, and hence detection of the presence in the specimen of cells infected with the deposited virus.

The glycoproteins or polypeptides immunologically cross-reactive therewith can be labelled by conventional procedures with $^{125}$I or $^{35}$S or $^{3}$H for use in radioimmunoassay, with fluorescein for fluorescent immunoassay, with enzyme for enzyme immunoassay, or with biotin for biotin-avidin linked assays. It can be employed labelled or unlabelled as desired, in competitive immunoassays, as well as in double antibody assays using two antibodies, either of the idiotype:antiidiotype variety or more particularly of the second antibody type using an anti-Fc antibody, or other assays.

Alternatively, the glycoproteins or polypeptides immunologically cross-reactive therewith could be immobilized on an insoluble phase, such as an insoluble resin, and detection of the anti-glycoprotein antibodies is carried out by measuring their binding to the insoluble phase. Insoluble phases also include latex particles, which, when coated with the novel glycoprotein or its immunologically cross-reactive polypeptides and subjected to anti-glycoprotein antibody, will agglutinate. Yet other insoluble phases include test tubes, vials, titration wells, and the like, to which the novel glycoprotein or its immunologically cross-reactive polypeptide can be bound, and antibody thereto detected by double antibody techniques or Protein-A dependent techniques.

The assay for antibodies which recognizes cell surface antigens induced by the deposited virus may utilize the glycoprotein or glycoproteins or the unglycosylated moiety of MW 120,000 daltons, 160,000 daltons and 90,000 daltons respectively in crude form, and is not limited to using these proteins in substantially pure form. For example, the glycoprotein(s) may be first substantially purified and then mixed together. Alternatively cruder mixtures can also be used.

The elements necessary for carrying out the diagnostic methodology described hereinbefore may be present in a kit. Such kit comprises a carrier being compartmentalized to receive therein one or more containers, which of said containers comprising one or more elements necessary to carry out the tests.

For example, the first container may contain one or both of the purified glycoproteins or its immunologically cross-reactive polypeptides in detectably labelled or in insolubilized form.

A second container may comprise anti IgG antibody, polyclonal or monoclonal, useful in double antibody binding assay, or elements needed for detection of the label on the glycoprotein or its immunologically cross-reactive polypeptides (e.g. chromogenic substrates).

Additional containers may comprise varying amounts of one of the glycoproteins or its immunologically cross-reactive polypeptides which can be used to prepare a standard curve into which experimental results can be interpolated. The materials may be present in the kit by themselves, in solution, freeze-dried, or in admixture with other inert materials, such as inert proteins, and the like.

The biological specimens tested may include blood, serum, lymphocytes, urine, tissues, saliva, feces, and the like. Of particular interest is the screening of blood or other tissue of African green monkeys to be used in vaccine production.

The following specific examples are intended to illustrate more fully the nature of the invention without acting as a limitation upon its scope.

EXAMPLES 1 AND 2

Assay of STLV-infected Macaque Serum with STLV-III Antigens

Figure 1:
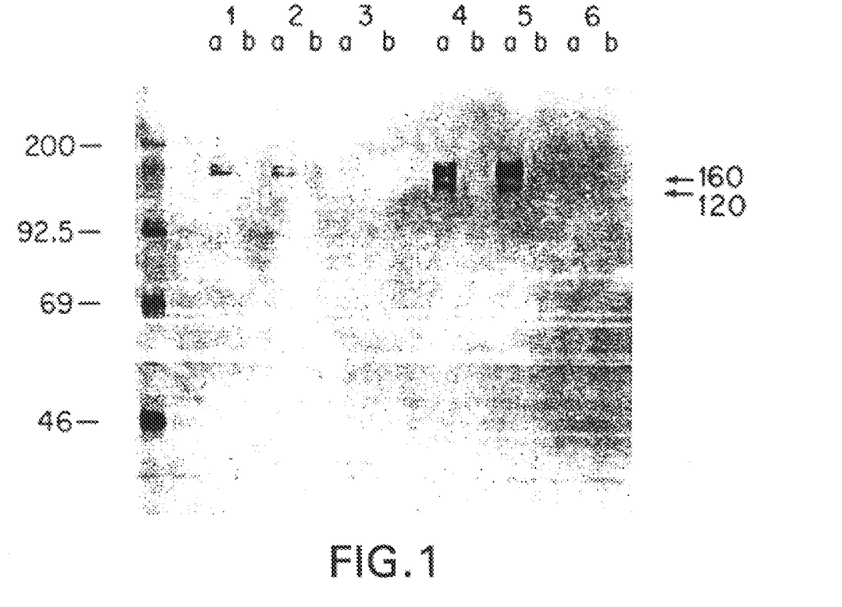
FIGS. 1–8 are photographs demonstrating immunoprecipitation of various serum samples with preparations of radiolabeled infected cell lysates with SDS/PAGE.
Figure 2:
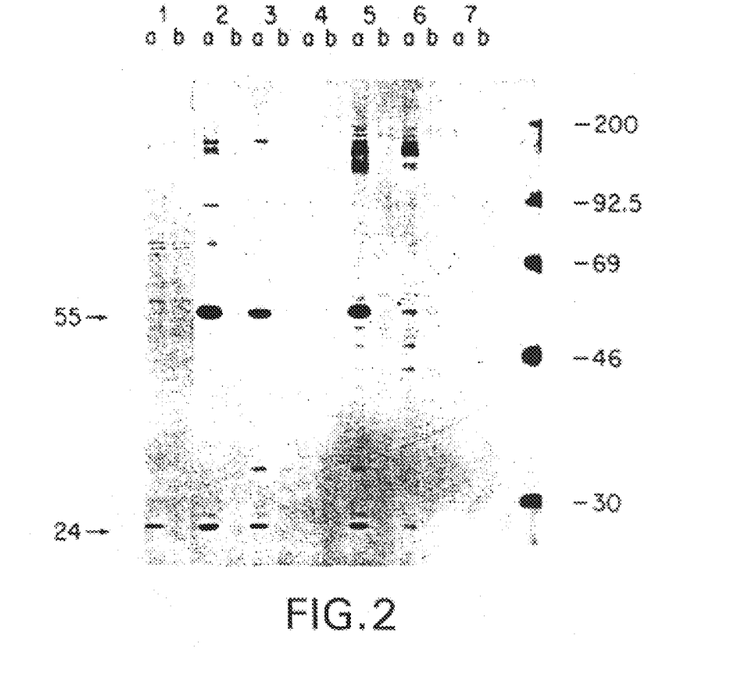
Figure 3:
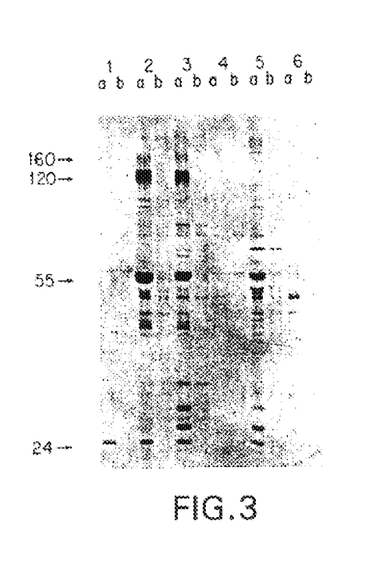
Figure 4:
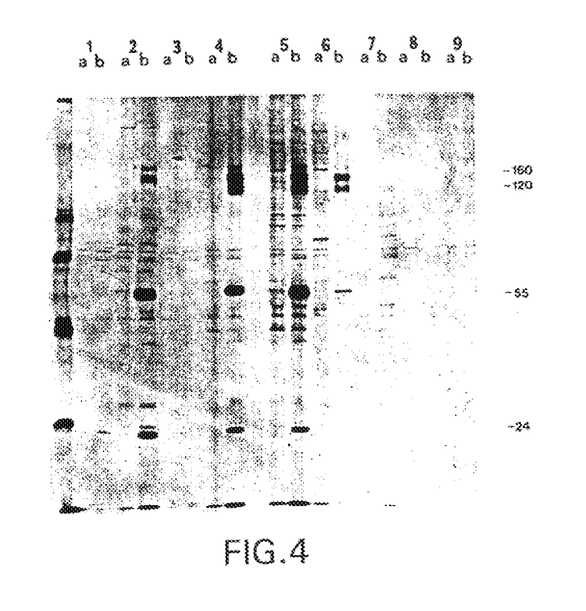
Figure 5:
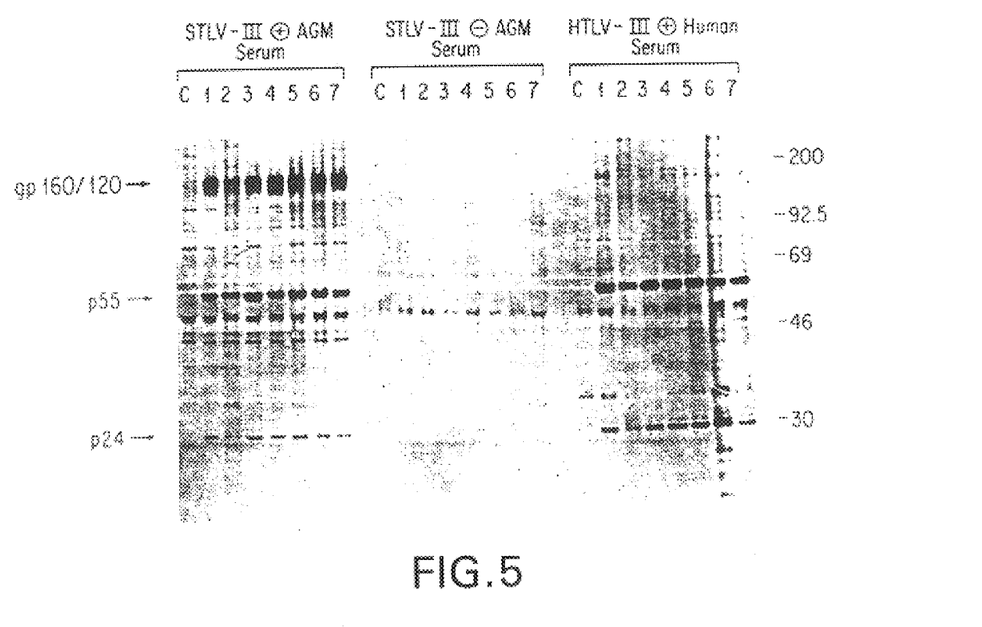

FIG. 1 shows the reactivity of various simian serum samples with the glycoprotein preparation of HUT-78/STLV-III$_{MAC}$ (lane a) and uninfected control HUT-78 (lane b). The glycoproteins are prepared from soluble cell lysates of the cells made with RIPA buffer as described below for FIG. 2, lacking sodium deoxycholate. The lysates are passed through a lentil-lectin-Sepharose Cl-4B (Pharmacia, Sweden) column at a ratio of $20\times10^6$ cells to 1 to 2 ml of undiluted lentil-lectin-Sepharose Cl-4B. The glycoproteins are eluted from the column with a buffer [0.15 M NaCl, 0.05 M tris-HCl, pH 7.2, 1% Triton X-100, and 0.2 methyl-α-D-mannoside]. The eluted bound fraction is reacted with 10 μl test sera that have been reacted to protein A beads (for example used in the general technique of Essex et al. [1983] Science 220:859). The sera used are: Lanes 1 and 2—human reference HTLV-III, positive serum; Lane 3—human reference HTLV-III, negative serum; Lanes 4 and 5—STLV-III positive macaque serum; Lane 6—STLV-III negative macaque serum. The immunoprecipitates are eluted from protein A beads boiling at 100° C. for 2 min. [sample buffer: 0.1 Cleland's reagent; 2% SDS; 0.08 M tris-HCl; pH 6.8; 10 percent glycerol; 0.2% bromophenol blue.] Samples are analyzed by SDS/PAGE in a 10.0 percent acrylamide resolving gel with a 3.5 percent stacking gel according to the discontinuous buffer system of Laemmli (1970) Nature (London) 227:680.

In FIG. 2, HUT-78/STLV-$III_{MAC}$ (lanes a) and HUT-78 (lanes b) are harvested at their peak of log-phase growth and are exposed to [$^{35}$S] cysteine [150 μCi/ml; specific activity, 1000 to 1050 Ci/mmole; New England Nuclear] for 8–10 hours. A soluble cell lysate is prepared by disruption of cells with RIPA buffer (0.15 M NaCl, 0.5 tris-HCl, pH 7.2, 1% sodium deoxycholate, 0.1% SDS). The lysate is then centrifuged for 1 h. at 100,000 g. The lysates are reacted with 10 μl of the following test sera: lane 1—monoclonal anti-p24 (HTLV-III); lanes 2 and 3—human reference HTLV-III, positive serum; lane 4—human reference HTLV-III, negative serum; lanes 5 and 6—macaque reference STLV-III positive serum; lane 7—macaque reference STLV-III negative serum.

In both FIGS. 1 and 2, the STLV-III-infected macaque serum recognizes the gp120/gp160 protein of STLV-$III_{MAC}$-infected cells.

EXAMPLE 3

Macaca STLV-III as Determined by HTLV-III Infected Cells

As shown in FIG. 3, the procedures described in example 2 were performed with HTLV-III-infected H9 cells using at lanes 1–5 the sera described for FIG. 2 at lanes 1–5 and using a representative macaque serum negative for STLV-III at lane 6.

EXAMPLES 4–6

STLV-III Detected in Simians by STLV-III Cell Proteins

In FIG. 4, the above-described procedures were performed using HUT 78 infected with the deposited virus and HUT 78(b) on the following serum samples: lane 1) monoclonal anti-p24 (HTLV-III); lane 2) human reference serum positive to HTLV-III; lane 3) human reference serum negative to HTLV-III; lane 4) macaque serum positive for STLV-III; lanes 5) and 6) AGM sera, positive for STLV-III; lane 7) AGM negative for STLV-III; lane 8) baboon serum negative for STLV-III; lane 9) chimpanzee serum negative for STLV-III. The 160, 120, 55, and 24 kd viral antigens of STLV-III are immunoprecipitated by positive macaque sera and by HTLV-III positive sera.

FIG. 5 demonstrates protein expression in HUT 78 cells infected with the deposited virus. The cell cultures were metabolically labeled with $^{35}$S cysteine and RIP-SDS/PAGE of whole cell lysates was performed with: a) an STLV-III antibody positive AGM serum sample; b) an STLV-III antibody negative AGM serum sample; and c) an HTLV-III antibody positive reference serum sample from a human with AIDS-related complex. Lanes designated C represent HUT 78 uninfected cells that were similarly labeled.

Specifically, the infected HUT 78 cells and uninfected controls were exposed to [$^{35}$S] cysteine [−150 Ci/ml; specific activity 1000–1050 Ci/mmole; New England Nuclear (NEN)] for four to six hours. A soluble cell lysate was prepared by disrupting cells with RIPA buffer (0.15 M NaCl, 0.05 M Tris-HCl, pH7.2, 1% sodium deoxycholate, and 0.1% SDS), and clearing by centrifugation for one hour at 100,000 g. Each group of cell lysates were reacted with 10 μl of the test sera bound to Protein A-sepharose CL-4B (Protein A-beads, Sigma). The immunoprecipitates were eluted in a sample buffer containing 0.1 M Cleland's reagent, 2% SDS, 0.08 M Tris-HCl, pH 6.8, 10% glycerol, and 0.2% bromophenol blue by boiling at 100° C. for two minutes. Samples were analyzed in a 10.0% acrylamide resolving gel with 3.5% stacking gel according to the discontinuous buffer system of Laemmli (1970) Nature 227:680.

As shown in FIG. 5, lysates from all seven cultures (lanes 1–7) showed bands of about 160 kd, 120 kd, 55 kd, and 24 kd, when reacted with serum from a reference antibody positive African green monkey. The same bands were not seen with lysate from uninfected HUT 78 cells (lane C). The proteins were also not detected when lysates from the seven infected cell cultures were reacted with a representative serum from an African green monkey that lacked antibodies to STLV-III. Serum from a human ARC patient recognized the 55 kd and 24 kd proteins and had faint reactivity to proteins of about 120 kd and 160 kd in lysates prepared from isolates 1–7 but the same bands were lacking in uninfected HUT 78 cells.

FIG. 6 shows immunoprecipitation by serum samples from seven different African green monkeys were reacted with cell lysates prepared from a cell line infected with the deposited virus (isolate 1) and uninfected HUT 78 cells (lanes 1–7). Infected (lanes a) and HUT 78 uninfected (lanes b) cell lysates were prepared as described above. Lanes $H^+$ contain serum samples from HTLV-III antibody positive human AIDS or ARC patients; lane $H^-$ contains a health control antibody negative human serum; lanes 1–7 are serum samples from African green monkeys; lanes 8–12 are serum samples from representative African green monkeys that were positive for antibodies to STLV-III$_{MAC}$, and lane 13 is a representative African green monkey serum that was negative for antibodies to STLV-III$_{MAC}$.

Figure 6:
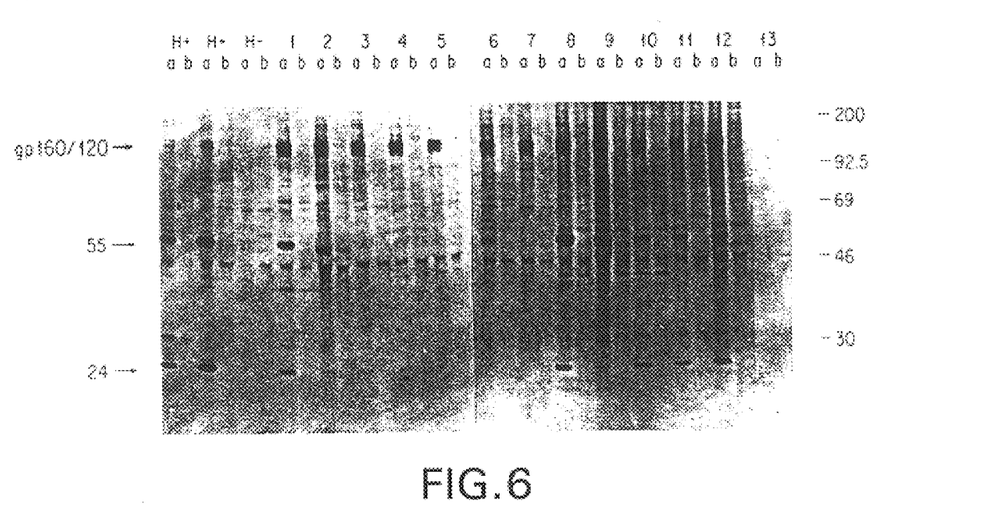

As shown in FIG. 6, sera from virus positive monkeys specifically precipitated the gp160/120, whereas only three of these serum samples additionally showed reactivity to the p55 and p24. Analysis of other African green monkeys sera has demonstrated a similar phenomenon where 11 of 42 (26%) STLV-III positive serum samples showed reactivity to the p55 and p24 in addition to reactivity to the gp160/120. Thus, the high molecular weight glycoproteins of this virus apparently are the most immunogenic species in infected monkeys.

STLV-III positive sera from African green monkeys were also analyzed for antibodies to HTLV/III/LAV proteins by RIP/SDS-PAGE where approximately 50% of these sera also showed reactivity to HTLV-III proteins. Other diagnostic assays were performed to detect this cross-reactivity reaction, in which the same serum samples were analyzed by ELISA to HTLV-III (Electronucleonics). STLV-III virus and antibody positive monkeys demonstrated antibodies to HTLV-III proteins by RIP SDS/PAGE in 5 of 8 serum samples whereas ELISA detected 2 of these 8 samples as HTLV-III positive. RIP and SDS/PAGE analysis appear to be more sensitive for the detection of the cross-reacting antibodies to the related virus in infected monkeys when compared to the HTLV-III kit ELISA.

EXAMPLE 7

Human Sera Reactivity With the Viral Proteins

Serum samples from healthy individuals (prostitutes or surgery patients) were obtained in Dakar, Senegal, and screened by a commercially available HTLV-III/LAV ELISA kit assay. ELISA-positive samples were then analyzed by RIP/SDS/PAGE as generally described above, to eliminate false positives.

All positive samples demonstrated strong reactivity to all of the STLV-III viral antigens, including p24, p55, and gp120/gp160. Only 27% of the samples demonstrated reactivity to all HTLV-III/LAV antigens; some of the samples failed to demonstrate any detectable antibodies to any major HTLV-III/LAV antigens, while others possessed antibodies only to p24 and p55 gag-related antigens. In all cases the reactivity to HTLV-III gp120 and gp160 was weak or non-existent compared to reactivity to STLV-III gp120/160. And there was a lack of detectable antibodies to gp41 when analyzed by Western blot analysis by the general technique of Barin et al. Lancet, ii, pp. 1387 et seq. (1985).

Figure 7:
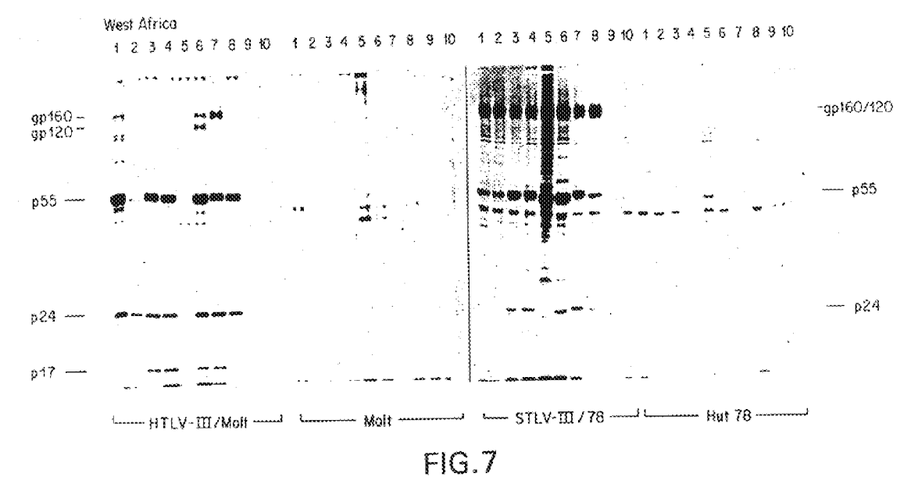

Representative serum samples from these West African individuals are shown in FIG. 7, with control serum samples from STLV-III antibody-positive African green monkeys. Specifically, serum samples from people residing in West Africa were analyzed by RIP-SDS/PAGE using the whole cell lysates as follows. Cells from HTLV-III (BH10 virus) infected Molt-3 cells, uninfected Molt-3 cells, Hut-78 infected STLV-III, and uninfected Hut-78 cells were harvested at their peak of log phase of growth and were exposed to ($^{35}$S) cysteine (–150 Ci/ml; specific activity 1000–1050 Ci/mmol; New England Nuclear (NEN)) for 4–6 hours. A soluble cell lysate was prepared by disrupting cells with RIPA buffer (0.15 M NaCl, 0.05 M Tris-HCl, pH 7.2, 1% sodium deoxycholate, and 0.1% SDS), and clearing by centrifugation for 1 hour at 100,000 g. Each group of cell lysates were reacted with 10 µl of the following test sera bound to Protein A-Sepharose Cl-4B (Protein A-beads, Sigma): (Lanes 1–2) STLV-III antibody positive African green monkeys; (lane 3) healthy West African control with antibodies to STLV-III; (lanes 4–8) sera from West African prostitutes with reactivity to STLV-III; (lane 9) STLV-III and HTLV-III seronegative prostitute from West Africa; and (lane 10) healthy West African control seronegative for STLV-III and HTLV-III.

Immunoprecipitates were eluted in a sample buffer containing 0.1 M Cleland's reagent, 2% SDS, 0.08 M Tris-HCl, pH 6.8, 10% glycerol, and 0.2% bromophenol blue by boiling at 100' for 2 minutes. Samples were anlayzed in a 10.0% acrylamide resolving gel with 3.5% stacking gel according to the discontinuous buffer system of Laemmli referenced above.

EXAMPLE 8

Identification of Antibodies to HTLV-IV

Figure 8:
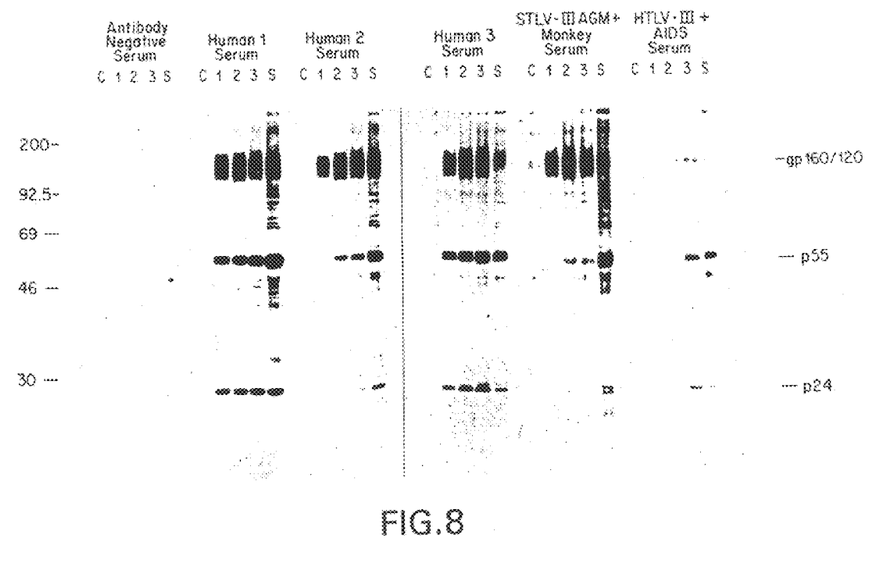

As shown in FIG. 8, whole cell lysates from three cell cultures infected with the deposited strains (lanes 1–3), STLV-III reference infected Hut-78 (S) and uninfected Hut-78 cells (C) were prepared as described above and analyzed by RIP-SDS/PAGE as follows. Each group of cell lysates were reacted with the following test sera: Negative human serum sample from West Africa, virus and antibody negative for STLV-III and HTLV-III, STLV-III antibody positive serum from human individual 1, STLV-III antibody positive serum from human individual 2, STLV-III antibody positive serum from human individual 3, reference STLV-III antibody positive serum from an African green monkey, and reference HTLV-III antibody positive serum from an AIDS patient.

Serum from a negative human control that lacked antibodies to both STLV-III and HTLV-III/LAV failed to recognize any specific proteins in any of the five lysates. Conversely, lysates from STLV-III-positive cultures 1, 2, and 3 demonstrated bands of about 160, 120, 55 and 24 kd when reacted with their own sera or serum from a reference STLV-III antibody positive African green monkey (lanes 1, 2, and 3). These bands were indistinguishable from proteins with similar electrophoretic mobility precipitated from reference STLV-III whole cell lysate (lanes S). These bands were not detectable when the same sera were reacted with uninfected Hut-78 cell lysates (lane C) or similarly prepared whole cell lysates from cultures derived from antibody negative people from West Africa. Serum from a reference U.S. AIDS patient recognized the 55 and 24 kd proteins of STLV-III and reacted similarly with the same proteins in cultures 1–3; only faint reactivity to the high molecular weight proteins, gp120/160, was observed.

Figure 9:
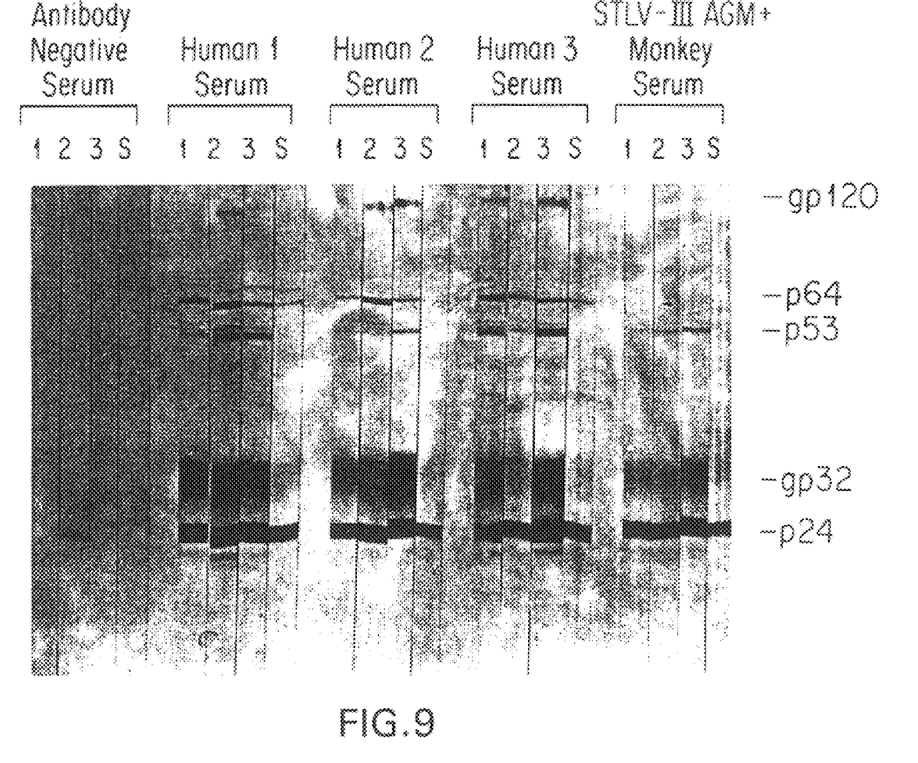
FIG. 9 is a photograph demonstrating Western blot analysis of described below.

As shown in FIG. 9, the viral antigens of STLV-III recognized by the Western blot procedure include the p24, p15, p53, p64, gp120 and gp32. p24 and p15 are gag-related and analogous to similar viral proteins of HTLV-III/LAV. A 120 kd protein has been demonstrated with some antibody positive serum samples; this protein is thought to be analogous to the HTLV-III/LAV gp120 which is less frequently detected by Western blot procedures but readily detected by HTLV-III/LAV antibody positive samples by RIP-SDS/PAGE. The smearing band at 32 kd using the Western blot technique of Barin et al. Lancet ii, p. 1387 (1985) correlates with a similar appearing 32 kd glycoprotein observed with lentil-lectin preparations and RIP-SDS/PAGE. The p32 protein may represent the transmembrane glycoprotein of the deposited virus, by analogy with the gp41 of HTLV-III/LAV. The p64 and p53 of the deposited virus are analogous to two pol gene products of HTLV-III/LAV, p53 and p64.

Western blots can be performed as demonstrated by the following example. Cell-free virus from cultures 1–3 as well as the deposited virus from a reference cell line was collected from supernatant fluid and subjected to Western blotting by the general technique of Barin et al. Strips were incubated with the same serum samples described in connection with FIG. 8. STLV-III antibody positive reference serum from an African green monkey showed reactivity with gp32, p24, p53, and p64 of STLV-III (FIG. 9). Similar proteins were recognized using serum samples from Western Africa Humans. Control antibody negative human serum failed to detect these bands in any of the four virus preparations.

As shown in FIG. 9, Western blot analysis was performed on preparations of cell cultures (lanes 1–3), and an STLV-III reference infected cell line (S). Each group of strips were reacted with: Negative serum human sample from West Africa, virus and antibody negative for STLV-III and HTLV-III, STLV-III antibody positive serum from human individual 1, STLV-III antibody positive serum from human individual 2, STLV-III antibody positive serum from human individual 3, and reference STLV-III antibody positive serum from an African green monkey.

IV. Vaccine

Since the deposited virus are immunologically cross-reactive with HTLV-III, and yet present data indicates reduced (or no) pathogenicity in their respective hosts, the deposited virus or a portion or derivative thereof could be used as a vaccine to protect against HTLV-III.

Specifically, using tryptic peptide analysis of the deposited viral peptide antigens, it is possible to determine the antigenic determinants which cross react with HTLV-III. Polypeptides that include these determinants can be synthesized, using organisms or cells engineered by recombinant DNA techniques. The resulting polypeptides can be recovered and included in a pharmaceutically acceptable carrier to innoculate individuals to raise protection against HTLV-III infection. Specifically, the conserved epitopes of the env protein of the deposited virus are candidate immunogens for HTLV-III/LAV vaccine development. U.S. Ser. No. 790,830, filed Oct. 23 or 24, 1985 by Kennedy, Dreesman and Essex, entitled Synthetic Peptides and Use for Diagnosis and Vaccination for AIDS and ARC, is hereby incorporated by reference in its entirety and discloses one method that could be used to derive a vaccine based on polypeptide antigens of the deposited virus.

What is claimed is:

1. An isolated polypeptide selected from the group consisting of:

(a) a cell-surface glycoprotein of m.w. of about 160,000;

(b) a cell-surface glycoprotein of m.w. of about 120,000;

(c) a gag protein of m.w. of about 55,000;

(d) a gag protein of m.w. of about 24,000; and (e) a glycoprotein of m.w of about 32,000;

wherein said polypeptide has said molecular weight when produced by a cell infected with a strain of the SIV virus, said cell deposited as ATCC 8942 or ATCC 8943 and wherein said polypeptide is not an HIV-I polypeptide having the same molecular weight as said isolated polypeptide.

2. The polypeptide of claim 1 wherein said infected cell is a progeny of one of the cell lines deposited as ATCC 8942 or ATCC 8943.

3. The isolated polypeptide according to claim 1, wherein said polylpeptide is selected from the group consisting of:

(a) a gag protein of m.w. of about 55,000; and (b) a gag protein of m.w. of about 24,000.

4. A cell lysate comprising a cell-surface glycoprotein of m.w. of about 160,000, wherein said glycoprotein of m.w. of about 160,000 has an antigenic determinant which, in common with an antigenic determinant of a protein produced by a cell infected with a strain of the SIV virus, said cell deposited as ATCC 8942 or ATCC 8943, will react with the same given antibody, and wherein said glycoprotein is not the HIV-I polypeptide having a m.w. of about 160,000.

5. The cell lysate of claim 4, further comprising a cell-surface glycoprotein of m.w. of about 120,000, wherein said glycoprotein of m.w. of about 120,000 has an antigenic determinant which, in common with an antigenic determinant of a protein produced by a cell infected with a strain of the SIV virus, said cell deposited as ATCC 8942 or ATCC 8943, will react with the same given antibody, and wherein said glycoprotein of m.w. of 120,000 is not the HIV-I polypeptide having a m.w. of about 120,000.

6. The cell lysate of claim 5, further comprising a gag protein of m.w. of about 55,000, wherein said gag protein of m.w. of about 55,000 has an antigenic determinant which, in common with an antigenic determinant of a protein produced by a cell infected with a strain of the SIV virus, said cell deposited as ATCC 8942 or ATCC 8943, will react with the same given antibody, and wherein said gag protein of m.w. of about 55,000 is not the HIV-I polypeptide having a m.w. of about 55,000.

7. The cell lysate of claim 6, further comprising a gag protein of m.w. of about 24,000, wherein said gag protein of m.w. of about 24,000 has an antigenic determinant which, in common with an antigenic determinant of a protein produced by a cell infected with a strain of the SIV virus, said cell deposited as ATCC 8942 or ATCC 8943, will react with the same given antibody, and wherein said gag protein of m.w. of about 24,000 is not the HIV-I polypeptide having a m.w. of about 24,000.

8. The cell lysate of claim 7, further comprising a glycoprotein of m.w. of about 32,000, wherein said glycoprotein of m.w. of about 32,000 has an antigenic determinant which, in common with an antigenic determinant of a protein produced by a cell infected with a strain of the SIV virus, said cell deposited as ATCC 8942 or ATCC 8943, will react with the same given antibody, and wherein said glycoprotein of m.w. of about 32,000 is not the HIV-I polypeptide having a m.w. of about 32,000.

9. An isolated cell-surface glycoprotein of m.w. of about 160 kD, wherein said protein has an antigenic determinant which, in common with an antigenic determinant of a protein also having a m.w. of about 160 kD produced by a cell infected with a strain of the SIV virus, said cell deposited as ATCC 8942 or ATCC 8943, will react with the same given antibody, and wherein said glycoprotein is not the 160 kD protein of HIV-I.

10. An isolated cell-surface glycoprotein of m.w. of about 120 kD, wherein said protein has an antigenic determinant which, in common with an antigenic determinant of a protein also having a m.w. of about 120 kD produced by a cell infected with a strain of the SIV virus, said cell deposited as ATCC 8942 or ATCC 8943, will react with the same given antibody, and wherein said glycoprotein is not the 120 kD protein of HIV-I.

11. An isolated gag protein of m.w. of about 55 kD, wherein said protein has an antigenic determinant which, in common with an antigenic determinant of a protein also having a m.w. of about 55 kD produced by a cell infected with a strain of the SIV virus, said cell deposited as ATCC 8942 or ATCC 8943, will react with the same given antibody, and wherein said gag protein is not the 55 kD protein of HIV-I.

12. An isolated gag protein of m.w. of about 24 kD, wherein said protein has an antigenic determinant which, in common with an antigenic determinant of a protein also having a m.w. of about 24 kD produced by a cell infected with a strain of the SIV virus, said cell deposited as ATCC 8942 or ATCC 8943, will react with the same given antibody, and wherein said gag protein is not the 24 kD protein of HIV-I.

13. An isolated glycoprotein of m.w. of about 32 kD, wherein said protein has an antigenic determinant which, in common with an antigenic determinant of a protein also having a m.w. of about 32 kD produced by a cell infected with a strain of the SIV virus, said cell deposited as ATCC 8942 or ATCC 8943, will react with the same given antibody, and wherein said glycoprotein is not the 32 kD protein of HIV-I.

* * * * *